United States Patent
Palma

(10) Patent No.: US 6,864,256 B2
(45) Date of Patent: Mar. 8, 2005

(54) METHODS FOR THE CONTROL OF INSECT PESTS

(75) Inventor: Kathleen G. Palma, McLeansville, NC (US)

(73) Assignee: Tria Specialty Products, LLC, Greensboro, NC (US)

( * ) Notice: Subject to any disclaimer, the term of this patent is extended or adjusted under 35 U.S.C. 154(b) by 0 days.

(21) Appl. No.: 10/232,628

(22) Filed: Aug. 29, 2002

(65) Prior Publication Data

US 2004/0043997 A1 Mar. 4, 2004

(51) Int. Cl.$^7$ .............................................. A61K 31/53
(52) U.S. Cl. ..................................... 514/245; 514/241
(58) Field of Search ................................. 514/241–246

(56) References Cited

U.S. PATENT DOCUMENTS

| | | | |
|---|---|---|---|
| 4,166,107 A | 8/1979 | Miller et al. | |
| 4,225,598 A | 9/1980 | Brechbuhler et al. | |
| 5,707,658 A | 1/1998 | Morgan et al. | |

OTHER PUBLICATIONS

WEBSTER'S II, New Riverside University Dictionary, pps 975 and 1324, 1984.*
Miller. R. W. et al., Southwestern Entomologist, 6(3), p. 272–278, 1981.*
Brake, J. et al., Poultry Science 70(9), pp. 1873–1875, Sep. 1991.*
Beadles et al., "The horn fly: methoprene in drinking water of cattle for control." J. Econ. Entomol., 68:781–785, 1975.
Bel et al., "Candidate Target Mechanisms of the Growth Inhibitor Cyromazine: Studies of Phenylalanine Hydroxylase, Puparial Amino Acids, and Dihydrofolate Reductase in Dipteran Insects." Arch. Ins. Biochem. Physiol., 45:69–78, 2000.
Friedal and McDonnell, "Cyromazine inhibits reproduction and larval development of the Australia sheep blow fly (Diptera: Calliphoridae)." J. Econ. Entomol., 78:868–873, 1985.

Harris et al., "Horn flies, stable flies, and house flies: development in feces of bovines treated orally with juvenile hormone analogues." J. Econ. Entomol., 66:1099–1102, 1973.

Harris et al., "Horn flies and stable flies: free–choice feeding of methoprene mineral blocks to cattle for control." J. Econ. Entomol., 67:384–386, 1974.

Miller et al., "Urine Delivery of Cyromazine for Suppressing House and Stable Flies (Diptera: Muscidae) in Outdoor Dairy Calf Hutches." J. Econ. Entomol., 89:689–694, 1996.

Schmidtmann et al., "Effect of Experimental Bedding Treatments on the Density of Immature *Musca domestica* and *Stomoxys calcitrans* (Diptera: Muscidae) in Outdoor Calf Hutches." J. Econ. Entomol., 82:1134–1139, 1989.

Skovmand, "Addition of the Larvicide Cyromazine to Pigfeed to Control Breeding of Houseflies (*Musca Domestica L.*) in the Manure." Intl. Pest Control, 30:10–13, 1988.

Skovmand and Brandt, "Fly control on mink farms," Ann. Rep. Danish Pest Infestation Lab., 43–44, 1981.

Webb and Chapman, "Cyromazine for the control of insecticide resistant houseflies (*Musca domestica L.*) in pig farrowing rooms," Int. Pest Control, 16–20, Jan./Feb. 1993.

* cited by examiner

*Primary Examiner*—Dwayne Jones
(74) *Attorney, Agent, or Firm*—Foley & Lardner LLP

(57) ABSTRACT

The present invention provides methods for the control of insect pests in the vicinity of feces or manure of a domestic animal. Such methods comprise orally administering cyromazine, wherein said administering results in the presence of an insecticidal amount of cyromazine in the feces of the animal being treated. The present invention further provides methods for inhibiting the development of fly larvae on feces or manure of a domestic animal. Such methods also comprise orally administering cyromazine, wherein said administering results in the presence of an insecticidal amount of cyromazine in the feces of the animal being treated.

37 Claims, No Drawings

METHODS FOR THE CONTROL OF INSECT PESTS

FIELD OF THE INVENTION

The present invention relates to methods for the control of insect pests in the vicinity of the feces or manure of a domestic animal. In a particular aspect, the invention relates to the oral administration of cyromazine that results in the presence of an insecticidal amount of cyromazine in the feces of a domestic animal.

BACKGROUND OF THE INVENTION

The following description is provided to assist the understanding of the reader. None of the information provided or references cited is admitted to be prior art to the present invention.

Insect pests that are frequently found in the vicinity of manure and the feces of domestic animals are annoyances and health hazards to the animals themselves and to people around such animals. In particular, flies, such as stable flies, horn flies, house flies, face flies and other flies which breed in manure, are common pests of mammals such as cattle, horses, sheep, goats, swine and poultry. If breeding of such insect pests remains uncontrolled, large numbers may quickly accumulate and may irritate and distress these animals to the degree that the animals become restless, hyperactive, and may even stop feeding temporarily. Distressed animals are also prone to illness and may frequently lose weight. Additionally, such insect pests are also vectors in the dissemination of a number of animal and human diseases and/or parasites. Thus, the control of insect pests is highly desirable, especially with personal or pet animals (such as horses and dogs), and where large numbers of animals are kept, such as on farms, feedlots, shipping yards, and the like.

Customarily, to control flies in barns and other animal shelters, the animals themselves, and their environment in general, are treated with pesticide-containing products. Though usually effective, these methods of control are time-consuming and expensive, especially if they require repetitive applications. Moreover, it is generally very difficult, if not impossible, to effectively treat animal feces and manure with pesticides to completely prevent flies from breeding therein.

A variety of insect growth regulators have successfully been used in the control of insect pests of domestic animals, particularly to control dung-breeding flies, as an alternative to traditional pesticides. Complete inhibition of development in manure has been achieved by administering insect growth regulators to cattle in ground feed (for example, juvenile hormone analogues, Harris et al., *J. Econ. Entomol.* 66:1099–1102, 1973), mineral blocks (for example, methoprene, in Harris et al., *J. Econ. Entomol.* 67:384–386, 1974), and drinking water (for example, methoprene, Beadles et al., *J. Econ. Entomol.* 68:781–785, 1975).

Cyromazine (2-cyclopropylamino-4,6-diamino-s-triazine) was developed as a new class of insect growth regulators derived from azidotriazine herbicides, after it was found to cause death to larvae or deformation to pupae (see, for example, U.S. Pat. No. 4,225,598; and Fridel and McDonell, *J. Econ. Entomol.* 78:868–873, 1985). U.S. Pat. No. 4,225,598 discloses that treating insect larvae representing the stage of eating and growing with cyromazine or salts thereof results in killing the freshly hatched larvae or preventing adults from hatching from the pupae. The mode of action of cyromazine appears to be distinct from that of classical insecticides, chemosterilants or juvenile hormone analogues, yet still remains uncertain (see, for example, Bel et al., *Arch. Ins. Biochem. Physiol.* 45:69–78, 2000).

Prior to the present invention, it was believed by those of skill in the art that cyromazine was excreted primarily in urine. Thus, the art has believed that in order to control flies in the vicinity of feces, the feces must be intermixed with urine to achieve insecticidal effectiveness. As such, the use of cyromazine has to date been limited to animals where anatomy, physiology and/or housing conditions inherently result in a mixing of urine and feces.

Cyromazine (also known as CGA-72662) is primarily used as a feed-through larvicide in chicken and as a foliar spray on agricultural crops. It is manufactured and formulated by Novartis under the trademark Larvadex®, developed especially for poultry, and presently marketed for fly control in caged-layer chicken manure. Larvadex® is provided as a 1% premix to be added to the chicken feed to achieve a concentration of 5 ppm in the feed. Because of both chicken anatomy, physiology (all chicken excreta are mixed in the cloaca before deposition), and the conditions under which chicken are housed, cyromazine excreted in chicken urine becomes mixed with manure and bedding, thereby inhibiting development of flies therein.

Efforts have been made to expand the use of cyromazine to other domestic animals. Studies have been performed to administer technical cyromazine to outdoor dairy calf hutches in the range of 0.1–1.0 mg/kg of body weight. Doses of 0.5–1.0 mg/kg were found to prevent the development of immature stages of flies in straw bedding. However, it was found that cyromazine in this system is excreted in calf urine, and thus, the insecticidal amount of cyromazine found in the straw bedding is attributable to saturation of the bedding with urine (see Schmidtmann et al., *J. Econ. Entomol.* 82:1134–1139, 1989; and Miller et al., *J. Econ. Entomol.* 89:689–698, 1996).

In another study, cyromazine was applied as a feed-through to fattening porkers to prevent house fly breeding in piggeries. In traditional pens with straw bedding, it was found that some adult flies did develop. The author states that this was probably due to uneven mixing of urine, manure and straw, because cyromazine is excreted mainly with the urine (see Skovmand, *Intl. Pest Control* 30:10–13, 1988). Thus, any insecticidal effect seen was attributable to cyromazine attaching to manure while draining through manure beds.

In another study, cyromazine added to the feed of mink was ineffective to prevent breeding of house flies (Skovmand and Brandt, *Ann. Rep. Danish Pest Infestation Lab.* 43–44, 1981). Again the author attributes the ineffectiveness of cyromazine to the fact that the mink urine contained 95% of all cyromazine excreted and the fact that mink tend to urinate and defecate at separate sites. The suggested solution is to ensure a mixing of dung and urine in farm animal houses to achieve effectiveness.

Thus, there remained a need in the art for the control of insect pests by treating animals that physiologically separate urine and feces, and are free to move about such that feces droppings are not confined to the same vicinity as urine. Various attempts to address this need have been made, but frequently involve labor-intensive and time-consuming tasks. For example, droppings and manure can be frequently collected and disposed of to prevent fly breeding. As another example, U.S. Pat. No. 5,707,658 provides a method whereby equine manure is treated with sodium bisulphate at least once a week to reduce flies, again a time-consuming activity. As an alternative, insecticides can be used, but in addition to being time-consuming, such applications (for example, sprays) present toxicity problems and environmental concerns.

Therefore, there still remains a need in the art for a simple method of controlling insect pests in low density animal housing and in the vicinity of isolated feces droppings, which is not associated with an additional time-consuming task to be performed by the owner of the domestic animal producing the waste.

SUMMARY OF THE INVENTION

It is an object of the present invention to provide the owner of a domestic animal with an easy method for the control of insect pests in the vicinity of the animal's feces. Accordingly, the present invention provides such a method, comprising orally administering cyromazine to the animal, wherein this administration results in the presence of an insecticidal amount of cyromazine in the animal feces. In preferred embodiments, the domestic animal is a mammal, such as a horse.

The present invention thus provides a convenient means for controlling insect pests such as flies, gnats and mosquitoes. The cyromazine can be easily orally administered using compositions and formulations such as a capsule, bolus, tablet, liquid or preferably by feed additive administration.

The presence of an insecticidal amount of cyromazine in the feces or manure prevents the development of fly larvae thereon. Thus, the invention further provides methods for inhibiting the development of fly larvae on feces or manure of a domestic animal.

DETAILED DESCRIPTION OF THE INVENTION

In accordance with the present invention, there are provided methods for the control of insect pests in the vicinity of the feces of a domestic animal. Such invention methods comprise orally administering cyromazine to said domestic animal, wherein said administering results in the presence of an insecticidal amount of cyromazine in said feces.

Cyromazine (2-cyclopropylamino-4,6-diamino-s-triazine) and salts thereof are disclosed in U.S. Pat. No. 4,225,598, hereby incorporated by reference herein in its entirety, and are commercially available from a variety of sources that are known to the agricultural community. Preferably, the cyromazine is obtained as technical product, at a purity of >90% active ingredient, more preferably >95%, most preferably >97%. The term "technical product" as used herein, refers to the usual form in which a pesticide is prepared and handled prior to formulation, usually at a high level of purity (greater than 95–98%) but not completely pure, since it may also contain small amounts of necessary additives.

Cyromazine can be used in particular for controlling a variety of insect pests, including hygiene pests and animal ectoparasites of the order Diptera, such as, for example, flies, gnats and mosquitoes. The methods of the present invention are particularly useful for control of insect pests of the following families: Muscidae (for example, house flies, stable flies, horn flies, and face flies), Mycetophilidae (for example, fungus gnats), Chloropidae (for example, eye gnats), Culicidae (for example, mosquitoes), Simuliidae (for example, black flies), Tipulidae (for example, crane flies), Calliphoridae (for example, blow flies), Gasterophilidae (for example, bot flies), and Tabanidae (for example, horse flies and deer flies). Accordingly, the present invention provides methods for the control of flies, wherein said flies are selected from the group consisting of stable flies, horn flies, house flies, face flies and a combination of two or more thereof.

These type of insect pests are a nuisance and health concern for all types of domestic animals, and persons coming into the vicinity of such animals. As used herein, a domestic animal may be any of various animals domesticated so as to live and breed in a tame (as opposed to wild) condition. In a preferred embodiment, the domestic animal is a mammal, most preferably a horse. In alternative embodiments, the mammal is selected from the group consisting of cattle, sheep, goats, pigs, ferrets, mink, dogs and cats. Because feces is not separable from urine in chicken, the methods of the present invention are not preferred in chicken.

The terms feces and manure are frequently used interchangeably. However, it is a beneficial feature of the present invention that an insecticidal amount of cyromazine is present in the feces of a domestic animal. As used herein, manure refers to refuse of stables and barnyards consisting of livestock excreta, which may contain urine in addition to feces. The use of cyromazine in domestic animals has heretofore been found to result in cyromazine being excreted primarily in the urine. Thus, when manure has been found to be insecticidal, it was due to the presence of urine as a component of the manure. This is the case in animals that are housed in small, confined areas, where urine becomes admixed with feces.

Surprisingly, the methods of the present invention disclosed herein provide oral administration of cyromazine such that an insecticidal amount of the active cyromazine is specifically present in the feces of the animal receiving the cyromazine. As such, feces that is excreted by the treated animal, but rarely comes into contact with urine from the same animal, is remarkably effective in completely preventing the development of hatched larvae into flies (see Example 2 infra). All prior art would tend to teach away from the oral administration of cyromazine to achieve an insecticidal amount in the feces of a treated animal because of the evidence and belief that it would be primarily excreted in urine. Thus, one of skill in the art, in light of all prior art, would not have expected to be able to effectively orally administer cyromazine, such that an insecticidal amount was present in the feces of a domestic animal.

The phrase "insecticidal amount" as used herein, refers to an amount of cyromazine that is effective in killing and/or preventing or inhibiting the development of insect eggs into larvae, and/or larvae into pupae, and/or larvae into adult insects, ultimately suppressing the total insect population in the vicinity of the feces of a treated animal. Preferably, the insecticidal amount prevents or inhibits the development of larvae into flies as measured in a bioassay as described infra. With respect to insect pests that feed on feces or manure, the present invention provides an insecticidal amount in the feces that prevents the development of fly larvae therein or thereupon. Preferably, an insecticidal amount is effective in killing and/or preventing or inhibiting development by at least 50% as compared to control untreated feces samples, more preferably >75%, and most preferably >90%.

To determine whether an insecticidal amount is present in the feces, a bioassay may be performed as described herein in Example 2. When the concentration of cyromazine in the feces is below an insecticidal amount, the feces sample will not be effective in preventing or inhibiting fly development in the bioassay. If this is the case, the dose administered to the animal can then be increased until a resulting feces sample (following dosing) is effective in the bioassay, thereby achieving an insecticidal amount of cyromazine in the feces.

By use of the term "control", it is meant to suppress the numbers of insects present in the vicinity of the animal feces. This can be accomplished by a variety of means, so long as the cyromazine comes into contact with the some developmental stage of insect pests, to kill or otherwise affect the development of eggs into larvae, larvae into pupae, or larvae into flies. Typically, in the control of manure-breeding pests, the pests feed from the feces or manure of the treated animal, and thereby come into contact with the insecticidal amount of cyromazine that is present in the feces.

Accordingly, the present invention also provides methods for inhibiting the development of fly larvae on feces or manure of a domestic animal, said method comprising oral administration of cyromazine to said domestic animal, wherein said administration results in the presence of an insecticidal amount of cyromazine in said feces. The phrase "inhibiting the development" as used herein refers to a reduction in the ultimate number of flies emerging from larvae in the vicinity of feces or manure from a treated animal, as compared to in the vicinity of feces or manure from an untreated animal. Preferably, the inhibition results in at least a 50% reduction in flies emerging from larvae (treated as compared to untreated), more preferably >75%, and most preferably >90%.

The term "vicinity" as used herein, refers to the physical environment surrounding the feces, whether accumulated in enclosed housing facilities, or as droppings out in open fields. Preferably, the insect pests are controlled within the living quarters of each individual housed animal treated with cyromazine, such as a stall in a barn or stable, typically an area of 100 square feet or less. Alternatively, out in open fields, insect pests are preferably controlled within a similar area, preferably within a radius of 10–20 feet around the feces, although there is no physical enclosure.

The methods of the present invention comprise orally administering cyromazine to a domestic animal. Cyromazine may be administered alone or in a formulation appropriate to the specific use envisaged and to the particular type of domestic animal being treated. A variety of methods can be used for oral administration, including capsule, bolus, tablet, liquid, or feed additive formulations.

Such formulations are prepared in a conventional manner in accordance with standard veterinary practice. Thus, capsules, boluses or tablets may be prepared or formulated by mixing the active substance with a suitable finely divided diluent or carrier additionally containing a disintegrating agent and/or binder such as starch, lactose, talc, magnesium stearate, gelatin, and the like. Oral drenches are prepared by dissolving or suspending the active ingredient cyromazine in a suitable medium. The term "formulated" also means, for example, preparing cyromazine in the form of a powder, a tablet, a granulate, a capsule, an emulsion, a foam, and other means known in the art. Liquid formulations may be also used to supplement drinking water, or to sprinkle or spread onto feed.

These formulations will vary with regard to the composition and concentration of active substance contained therein depending on the type of domestic animal to be treated and factors such as the body weight of the animal. A typical dose range of the active ingredient cyromazine according to the methods of the present invention is 0.1–5.0 mg/kg of body weight of the animal per day. Preferably the oral administration comprises daily administration at about greater than 0.5 mg/kg, more preferably at about greater than 0.75 mg/kg, more preferably at about greater than 1.0 mg/kg, at about greater than 1.1 mg/kg, at about greater than 1.2 mg/kg, and most preferably at about greater than 1.25 mg/kg.

In a presently preferred embodiment oral administration comprises daily administration of cyromazine during fly season, as determined by the geographical and environmental location of the domestic animal being treated. As an alternative embodiment, cyromazine may be administered every other day, or in 3, 4, 5, 6, or 7 day intervals during the desired time period for controlling insect pests.

Cyromazine may be conveniently administered orally as a feed additive, such that the animal ingests the dosage of cyromazine with their feed. The active ingredient cyromazine may simply be used as a top-dressing for feed, i.e., simply by sprinkling or spreading technical product over feed to be consumed by the animal being treated. Alternatively, the cyromazine may be intermixed with the animal feed, for example, a concentrated feed additive or premix may be prepared for mixing with the normal animal feed. The formulation of veterinary additives in animal feed is an extremely well-known art. It is usual to formulate the compound first as a premix in which the active ingredient is dispersed in a liquid or particulate solid carrier. The premix may conveniently contain a concentrated amount of cyromazine and "diluted" down to the desired concentration in the feed. As is known in the art, many active ingredients can be hydrolyzed or degraded by constituents of animal feed. If the cyromazine in the chosen mix is likewise susceptible to degradation, it may be formulated in protective matrices such as gelatin before addition to the premix.

Alternatively, feed may be specially formulated to contain the cyromazine. Another variation of a feed additive comprises supplementing the domestic animal's water supply with cyromazine, either with a solid or liquid form of cyromazine. In addition, domestic animals frequently ingest supplemental foodstuffs that may be combined with cyromazine. A "supplemental foodstuff" as used herein, refers to any food product or supplement consumed by the animal in addition to its regular feed. As an example, treats such as sugar cubes or biscuits can be treated with cyromazine, or formulated to contain with cyromazine, and fed to the animal to achieve the oral administration.

Accordingly, a number of methods known in the art can be used for administering a formulated or pure active ingredient orally. The preparation does not necessarily have to be administered to the animal directly; it may be most convenient to mix it with the animal's feed as discussed above. In addition to containing adjuvants conventionally employed in the art of formulation, the compositions to be administered orally may of course contain further additives which stimulate voluntary ingestion by the animal, e.g. suitable scents or flavorings. Owing to its simplicity, oral administration is one of the preferred objects of the present invention.

As further examples of methods of oral administration, one of skill in the art could provide cyromazine in chewable tablets, water-dissolvable capsules or tablets, water-soluble compounds applied with a dropper into water or materials applied in any form onto feed. The cyromazine compositions or formulations may also contain further ingredients, such as stabilizers, antifoams, viscosity regulators, binders, tackifiers as well as other active ingredients for obtaining special effects. Materials known from veterinary practice as being suitable for being administered orally may be employed as formulation assistants.

Suitable carriers are especially fillers, such as sugars (for example lactose, saccharose, mannitol or sorbitol), cellulose preparations and/or calcium phosphates (for example tricalcium phosphate or calcium hydrogen phosphate), also binders, such as starch pastes using, for example, corn, wheat, rice or potato starch, gelatin, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragee cores can be provided with suitable coatings that may be resistant to gastric juices, e.g., concentrated sugar solutions which may contain gum arabic, talc, polyvinylpyrrolidone, polyethylene glycol and/or titanium dioxide, or lacquer in suitable organic solvents or solvent mixtures or, for the production of coatings that are resistant to gastric juices, solutions of suitable cellulose preparations, such as acetylcellulose phthalate or hydroxypropylmethylcellulose phthalate. Colorings, flavorings or pigments can be added to the tablets or dragee coatings, for example for identification purposes or to indicate different doses of active ingredient.

Further orally administrable preparations are dry-filled capsules consisting of gelatin and also soft, sealed capsules consisting of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilizers. In soft capsules, the active ingredient is preferably dissolved or suspended in suitable liquids, such as fatty oils, paraffin oil or liquid polyethylene glycols, it being possible also to add stabilizers. Preferred are, inter alia, capsules that can be easily bitten through or swallowed without being chewed.

The formulations of the present invention can be manufactured in any manner known to those of skill in the art, for example, by means of conventional mixing, granulating, confectioning, dissolving or lyophilizing processes. For example, pharmaceutical preparations for oral administration can be obtained by combining the active ingredient with solid carriers, optionally granulating a resultant mixture, and processing the mixture or granulate, if desired or necessary after the addition of suitable adjuncts, to form tablets or dragee cores.

The invention will now be described in greater detail by reference to the following non-limiting examples.

EXAMPLE 1

Cyromazine Administration and Manure Collection

Cyromazine (2-cycloproplyamino-4,6-diamino-s-triazine) was obtained as a purified chemical composition at greater than 98% cyromazine (technical cyromazine). 600 mg of cyromazine was orally administered to each horse daily by top-dressing horse feed, for a continuous daily administration during fly season. In this example, horses residing in North Carolina, U.S. were treated during the local fly season, lasting approximately March through October of the calendar year.

In one study, cyromazine administration was stopped, and 5 manure samples were obtained from the same horse at 24, 48, 72, 96 and 120 hours post-dosing to monitor the duration of cyromazine at an insecticidal amount in the feces. In another study, single manure samples were collected from each individual horse (n=4) <24 hours after dosing with cyromazine, i.e., before another daily dose was given. Untreated control horse manure was collected from a nearby horse ranch. Samples were shipped and kept in the refrigerator until the house fly bioassay was set-up. Cyromazine was well tolerated at this dosage, and no side effects were seen.

EXAMPLE 2

House Fly Bioassay

Preparation of Eggs/Larval Hatch

Approximately fifty (50) *Musca domestica* (Hilmer Strain) eggs <24 hours old were counted and placed on filter paper discs in each of four replicates (rep) per cyromazine treatment group or control. Each replicate was covered with a paper towel and placed in the environmental chamber at 80° F. (27° C.), 80% relative humidity and a 14:10 (light:dark) photoperiod. The eggs were scored for larval hatch after two days and a layer of wood shavings added as a moisture barrier and a dry substrate for pupation.

Adult Fly Emergence from Larvae Exposed to Cyromazine in Feces

The replicates containing hatched larvae were then returned to the environmental chamber in the presence of the test feces samples to determine the insecticidal effect of the cyromazine in the feces. Adult house fly emergence from larvae was determined after 3 weeks.

Calculations

The percent larval hatch, adult fly emergence and corrected percent effect were calculated and recorded. The percentage of eggs hatching is calculated as the mean number of eggs hatched after 2 days per test divided by 50 (the total eggs input), and multiplied by 100. The percentage of adult fly emergence from larvae hatched (% larvae emerging as flies) is calculated as the mean number of adult flies emerging after 3 weeks per test divided by the mean number of larvae hatching on test day 2, and multiplied by 100. The percentage of larvae not developing is calculated as the mean number of larvae not developing per test divided by the mean number of larvae hatching on test day 2, and multiplied by 100. Thus, the data in Table 2 refers back to the data in Table 1, and the data in Table 4 refers back to the data in Table 3.

Insecticidal Activity of Feces From Cyromazine Treated Horses

In the first study, where the same horse was sampled at 5 different time points, cyromazine treatment completely inhibited adult fly emergence from the larvae that did hatch in the first portion of the test (see Table 2). An insecticidal amount of cyromazine was present in the feces obtained at 24, 48, 72, 96 and 120 hours post-dosing. Only 1 fly (0.2%) emerged from the 120 hour sample (4 reps). Control emergence was 75.2% for the untreated control samples (n=4).

TABLE 1

Larval Hatch/50 Eggs

| Time post-dosing | Rep 1 | Rep 2 | Rep 3 | Rep 4 | Σ | Mean | % Eggs Hatching |
|---|---|---|---|---|---|---|---|
| Control | 43 | 37 | 48 | 37 | 165 | 41.25 | 82.5 |
| 24 hours | 40 | 35 | 42 | 48 | 165 | 41.25 | 82.5 |
| 48 hours | 31 | 21 | 30 | 33 | 115 | 28.75 | 57.5 |
| 72 hours | 27 | 35 | 18 | 21 | 101 | 25.25 | 50.5 |
| 96 hours | 40 | 38 | 38 | 34 | 150 | 37.50 | 75.0 |
| 120 hours | 38 | 25 | 31 | 28 | 122 | 30.50 | 61.0 |

TABLE 2

Adult Fly Emergence from Larvae Hatched (from Table 1)

| Time post-dosing | Rep 1 | Rep 2 | Rep 3 | Rep 4 | Σ | % Larvae Emerging as Flies | # Larvae not Developing | % Larvae not Developing |
|---|---|---|---|---|---|---|---|---|
| Control | 29 | 31 | 34 | 30 | 124 | 75.2 | 41 | 24.8 |
| 24 hours | 0 | 0 | 0 | 0 | 0 | 0 | 165 | 100.0 |
| 48 hours | 0 | 0 | 0 | 0 | 0 | 0 | 115 | 100.0 |
| 72 hours | 0 | 0 | 0 | 0 | 0 | 0 | 101 | 100.0 |
| 96 hours | 0 | 0 | 0 | 0 | 0 | 0 | 150 | 100.0 |
| 120 hours | 1 | 0 | 0 | 0 | 1 | 0.8 | 121 | 99.8 |

In the second study, where different horses (n=4) were all sampled at <24 hours post-dosing, cyromazine treatment was again able to completely inhibit adult fly emergence from the larvae that did hatch in the first portion of the test (see Table 4). All 4 treatment groups (horses) demonstrated 100% inhibition of house fly development in this bioassay system. Control emergence was 66.3% for the untreated control samples (n=4), which was lower than expected. (These were field-collected samples, so some pathogens or parasites may have been in the sample.)

TABLE 3

Larval Hatch/50 Eggs

| Horse | Rep 1 | Rep 2 | Rep 3 | Rep 4 | Σ | Mean | % Eggs Hatching |
|---|---|---|---|---|---|---|---|
| Control Youngs | 48 | 46 | 41 | 43 | 178 | 44.50 | 89 |
| Precious | 49 | 37 | 44 | 49 | 179 | 44.75 | 89.5 |
| Fancy | 47 | 33 | 32 | 35 | 147 | 36.75 | 73.5 |
| Phalete | 45 | 37 | 57* | 35 | 167* | 41.75 | 83.5 |
| Barney | 25 | 33 | 43 | 32 | 133 | 33.25 | 66.5 |

*Because 57 larvae were counted from an input of 50 eggs, the sum (Σ) has been decreased by 7 to reflect this inconsistency, likely due to an inaccurate input due to technical difficulty in counting eggs.

TABLE 4

Adult Fly Emergence from Larvae Hatched (from Table 3)

| Horse | Rep 1 | Rep 2 | Rep 3 | Rep 4 | Σ | % Larvae Emerging as Flies | # Larvae not Developing | % Larvae not Developing |
|---|---|---|---|---|---|---|---|---|
| Control Youngs | 29 | 29 | 35 | 25 | 118 | 66.3 | 60 | 33.7 |
| Precious | 0 | 0 | 0 | 0 | 0 | 0 | 179 | 100.0 |
| Fancy | 0 | 0 | 0 | 0 | 0 | 0 | 147 | 100.0 |
| Phalete | 0 | 0 | 0 | 0 | 0 | 0 | 167 | 100.0 |
| Barney | 0 | 0 | 0 | 0 | 0 | 0 | 133 | 100.0 |

The results clearly indicate a high degree of insecticidal activity attributable to the presence of cyromazine in the manure samples obtained from horses who were orally administered cyromazine. All samples were immediately collected to prevent any mixing or urine with feces from the treated horses. Therefore, the insecticidal activity detected in this bioassay is directly attributable to the cyromazine in the feces of the treated horses.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The disclosure of all publications cited above are expressly incorporated herein by reference, each in its entirety, to the same extent as if each were incorporated by reference individually.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

That which is claimed is:

1. A method for the control of insect pests in the vicinity of the feces of an uncaged domestic animal, said method comprising orally administering cyromazine to said domestic animal, wherein said administering results in the excretion of an insecticidal amount of cyromazine in feces, not admixed with urine, of said domestic animal.

2. A method according to claim 1, wherein said uncaged domestic animal is a horse.

3. A method according to claim 1, wherein said insect pests are flies.

4. A method according to claim 3, wherein said flies are selected from the group consisting of stable flies, horn flies, house flies, face flies and a combination of two or more thereof.

5. A method according to claim 3, wherein said insecticidal amount of cyromazine prevents the development of fly larvae in said feces or manure.

6. A method according to claim 1, wherein said insect pests are gnats.

7. A method according to claim 1, wherein said oral administration is accomplished by capsule, bolus, tablet, liquid, or feed additive administration.

8. A method according to claim 7, wherein said feed additive comprises top-dressing feed with cyromazine.

9. A method according to claim 7, wherein said feed additive comprises intermixing feed with cyromazine.

10. A method according to claim 7, wherein said feed additive comprises fomulating feed containing cyromazine.

11. A method according to claim 7, wherein said feed additive comprises supplementing said domestic animal's water supply with cyromazine.

12. A method according to claim 7, wherein said feed additive comprises combining said domestic animal's supplemental foodstuff with cyromazine.

13. A method according to claim 1, wherein said oral administration comprises daily administration of cyromazine during fly season.

14. A method according to claim 1, wherein said oral administration comprises administration of cyromazine every other day during fly season.

15. A method according to claim 13, wherein said oral administration comprises daily administration of cyromazine at about greater than 0.5 mg/kg body weight.

16. A method according to claim 13, wherein said oral administration comprises daily administration of cyromazine at about greater than 0.75 mg/kg body weight.

17. A method according to claim 13, wherein said oral administration comprises daily administration of cyromazine at about greater than 1.0 mg/kg body weight.

18. A method according to claim 13, wherein said oral administration comprises daily administration of cyromazine at about greater than 1.25 mg/kg body weight.

19. A method for inhibiting the development of insect pests in the vicinity of the feces or manure of a domestic animal selected from the group consisting of horses, dogs and cats, said method comprising oral administration of cyromazine to said domestic animal, wherein said administration results in the excretion of an insecticidal amount of cyromazine in said feces, not admixed with urine, of said domestic animal.

20. A method for the control of insect pests in the vicinity of the feces or manure of a horse, said method comprising orally administering cyromazine to said horse, wherein said administering results in the physiological excretion in the horse's feces of an insecticidal amount of cyromazine.

21. A method according to claim 20, wherein said insect pests are flies.

22. A method according to claim 21, wherein said flies are selected from the group consisting of stable flies, horn flies, house flies, face flies and a combination of two or more thereof.

23. A method according to claim 21, wherein said insecticidal amount of cyromazine prevents the development of fly larvae in said feces or manure.

24. A method according to claim 20, wherein said insect pests are gnats.

25. A method according to claim 20, wherein said oral administration is accomplished by capsule, bolus, tablet, liquid, or feed additive administration.

26. A method according to claim 25, wherein said feed additive comprises top-dressing feed with cyromazine.

27. A method according to claim 25, wherein said feed additive comprises intermixing feed with cyromazine.

28. A method according to claim 25, wherein said feed additive comprises formulating feed containing cyromazine.

29. A method according to claim 25, wherein said feed additive comprises supplementing said horse's water supply with cyromazine.

30. A method according to claim 25, wherein said feed additive comprises combining said horse's supplemental foodstuff with cyromazine.

31. A method according to claim 20, wherein said oral administration comprises daily administration of cyromazine during fly season.

32. A method according to claim 20, wherein said oral administration comprises administration of cyromazine every other day during fly season.

33. A method according to claim 20, wherein said oral administration comprises administration of cyromazine at an interval selected from the group consisting of 3 days, 4 days, 5 days, 6 days, and 7 days.

34. A method according to claim 20, wherein said oral administration comprises administration of cyromazine at a dose of about greater than 0.5 mg/kg body weight.

35. A method according to claim 20, wherein said oral administration comprises administration of cyromazine at a dose of about greater than 0.75 mg/kg body weight.

36. A method according to claim 20, wherein said oral administration comprises administration of cyromazine at a dose of about greater than 1.0 mg/kg body weight.

37. A method according to claim 20, wherein said oral administration comprises administration of cyromazine at a dose of about greater than 1.25 mg/kg body weight.

* * * * *

UNITED STATES PATENT AND TRADEMARK OFFICE
CERTIFICATE OF CORRECTION

PATENT NO. : 6,864,256 B2
DATED : March 8, 2005
INVENTOR(S) : Kathleen G. Palma

It is certified that error appears in the above-identified patent and that said Letters Patent is hereby corrected as shown below:

<u>Title page,</u>
Item [73], Assignee, change "Tria" to -- Triad --.

Signed and Sealed this

Twenty-third Day of August, 2005

JON W. DUDAS
*Director of the United States Patent and Trademark Office*